US009283204B2

(12) United States Patent
Ip et al.

(10) Patent No.: US 9,283,204 B2
(45) Date of Patent: Mar. 15, 2016

(54) COMPOSITION FOR TREATING NEURODEGENERATIVE DISEASE OR NEUROPATHOLOGICAL CONDITION

(75) Inventors: Nancy Yuk Yu Ip, Hong Kong (CN); Kenny Ka Kin Chung, Hong Kong (CN); Fanny Chui Fun Ip, Hong Kong (CN); Guangmiao Fu, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 153 days.

(21) Appl. No.: 13/814,555

(22) PCT Filed: Aug. 10, 2011

(86) PCT No.: PCT/CN2011/001325
§ 371 (c)(1),
(2), (4) Date: Feb. 6, 2013

(87) PCT Pub. No.: WO2012/019435
PCT Pub. Date: Feb. 16, 2012

(65) Prior Publication Data
US 2013/0137762 A1   May 30, 2013

Related U.S. Application Data

(60) Provisional application No. 61/344,505, filed on Aug. 10, 2010.

(51) Int. Cl.
*A01N 43/16* (2006.01)
*A61K 31/35* (2006.01)
*A61K 31/353* (2006.01)
*A61K 36/9062* (2006.01)
*C07D 311/30* (2006.01)
*C07D 311/32* (2006.01)

(52) U.S. Cl.
CPC ........... *A61K 31/353* (2013.01); *A61K 36/9062* (2013.01); *C07D 311/30* (2013.01); *C07D 311/32* (2013.01)

(58) Field of Classification Search
None
See application file for complete search history.

(56) References Cited

U.S. PATENT DOCUMENTS

2005/0042311 A1*   2/2005   Lee et al. ................ 424/767

FOREIGN PATENT DOCUMENTS

KR   10-20090078493 A   7/2009
KR   20090078493 A   *   7/2009   ............. A61K 31/35

OTHER PUBLICATIONS

Fiskum et al. (Annals of the New York Academy of Sciences, 2003, 991, 111-119, Abstract only).*
Jaganathan et al. (Journal of Biomedicine and Biotechnology, May 13, 2009, 1-13).*
Carpentieri et al, "Antioxidant and antiapoptotic properties of melatonin restore intestinal calcium absorption altered by menadione", *Molecular and Cellular Biochemistry* (2013).
Willis, Gregory L., "Parkinson's Disease as a Neuroendocrine Disorder of Ciradian Function: Dopamine-Melatonin Imbalance and the Visual System in the Genesis and Progression of the Degenerative Process", *Reviews in the Neurosciences*, 19(4-5), 245-316 (2008).
Bi et al, "Salvianolic acid A positively regulates PTEN protein level and inhibits growth of A549 lung cancer cells", *Biomedical Reports*, 1(2), 213-217 (2013).
Zhang et al, "Salvianolic acid A protects human SH-SY5Y neuroblastoma cells against $H_2O_2$-induced injury by increasing stress tolerance ability", *Biochemical and Biophysical Research Communications*, 421(3), 479-83 (2012).
Andrabi et al., "Direct inhibition of the mitochondrial permeability transition pore: a possible mechanism responsible for anti-apoptotic effects of melatonin", *FASEB Journal*, 10.1096/fj.03-1031 fje (2004).
Lim et al., "Induction of p53 contributes to apoptosis of HCT-116 human colon cancer cells induced by the dietary compound fisetin" *Am J Physiol Gastrointest Liver Physiol* 296: G1060-G1068 (2009).
Zheng et al., "Suppressive effects of flavonoid fisetin on lipopolysaccharide-induced microglial activation and neurotoxicity", *International Immunopharmacology*, 8, 484-494 (2008).

* cited by examiner

*Primary Examiner* — Dennis Heyer
*Assistant Examiner* — Daniel M Podgorski
(74) *Attorney, Agent, or Firm* — Leydig, Voit & Mayer, Ltd.

(57) ABSTRACT

This invention relates to extracts and refined fractions of a traditional Chinese medicinal herb, *Alpinia officinarum* (AO), components thereof, and the use of such compounds and compositions to treat neurodegenerative or neuropathological conditions or to inhibit aggregation of a-synuclein.

10 Claims, 14 Drawing Sheets

A

B

A

TE – total extract, WA - water

B 1.1: galangin 1.2: 4'-methoxykaempferol 1.3: dihydrogalangin 1.4: galangin-3-methyl ether

COMPOSITION FOR TREATING NEURODEGENERATIVE DISEASE OR NEUROPATHOLOGICAL CONDITION

BACKGROUND OF THE INVENTION

Parkinson's disease (PD) is the second most common progressive neurodegenerative disorder. The clinical manifestations of PD include resting tremors, rigidity, bradykinesia and postural instability with cognitive and emotional disorders. The primary characteristic pathology of PD is the loss of dopaminergic neurons in the substantia nigra pars compacta and the presence of intracytoplasmic inclusions known as Lewy bodies. The etiology and the pathogenesis of PD are not completely known but recent evidence suggest that environmental and genetic factors might account for the progression of this disease (Schapira, *Lancet Neurol.*, 7: 97-109 (2008)). PD is considered to be a sporadic disease but recently several susceptive genes have been identified to be associated with familial forms of PD. Three missense point mutations (A53T, A30P and E46K) and genomic duplication or triplication of the α-synuclein gene have been reported as a cause of familial PD (Lee and Trojanowski, *Neuron*, 52: 33-38 (2006)).

α-synuclein is a protein that is predominately expressed in neurons, especially at synaptic terminals. The functions of α-synuclein are not well defined but it is reported to have potential roles in synaptic function and neural plasticity. A knockout animal model, used to examine the role of α-synuclein, was observed to be viable and have normal synaptic structure and brain morphology. These studies indicate that α-synuclein may modulate dopamine release, synthesis or storage. It may also act as a regulator of synaptic plasticity (Lotharius and Brundin, *Hum. Mol. Genet.*, 11: 2395-407 (2002)).

In addition to PD, α-synuclein has also been identified as a major component of Lewy bodies and Lewy neurites in dementia with Lewy bodies (DLB), Alzheimer's disease (AD), pure autonomic failure (PAF), multiple system atrophy (MSA), and other neurodegenerative disorders (Lippa et al., *Am. J. Pathol.*, 153: 1365-70 (1998), Marti et al, *Mov. Dis.*, 18:S21-S27 (2003), Norris et al., *Curr. Top. Dev. Biol.*, 60: 17-54 (2004)). The pathological α-synuclein exists as insoluble, filamentous aggregates containing abnormally nitrated, phosphorylated, and ubiquitinated residues in Lewy bodies and Lewy neurites. This new discovery has established α-synucleinopathy as an essential pathogenic feature of neurodegenerative diseases. It has been suggested that α-synuclein proteins have high propensity to adopt various conformations, with a strong tendency to self-aggregate into oligomers, which further aggregate into fibrils that are deposited as Lewy bodies and other similar pathologies. The mutant forms of α-synuclein are more inclined to aggregate as demonstrated in vitro and in animal models (Conway et al, *Nat. Med.*, 4: 1318-1320 (1998); Giasson et al, *Neuron*, 34: 521-233 (2002)).

Additionally, it is thought that α-synuclein protein levels increase with age in the human substantia nigra (Li et al., *J. Neurosci.*, 24: 9400-9409 (2004)). The connection between α-synuclein and neurodegenerative phenotypes in human patients and animal models strongly highlight the significance of the expression levels and the abnormal aggregation of this protein in the pathogenesis of PD. A53T α-synuclein transgenic mice under the control of the mouse prion-related protein promoter shows a marked and ultimately fatal motor paralysis with advancing age. Their motor neurons exhibit axonal degeneration near fibrillary α-synuclein inclusions, which reminisce part of the structure of the Lewy bodies (Giasson et al., *Neuron*, 34: 521-233 (2002)). A wealth of evidence suggest that the aggregated insoluble oligomer (protofibril) of α-synuclein plays an important role in the pathogenesis of PD. The assembly of the misfolded proteins in the form of oligomers leads to synaptic dysfunction, neuronal apoptosis and brain damage and underlies the pathogenesis of PD. Lansbury and co-worker demonstrated that α-synuclein protofibril forms elliptical or circular amyloid pores that can puncture the cell membrane which results in the release of the cell contents and cell death (Lashuel et al., *Nature*, 418: 291 (2002)).

Currently, there are no specific treatments that either halts or reverses the progression of PD. Commercially available drugs only relieve the symptoms of the disease to improve quality of life in PD patients. Since there are a wide range of symptoms and complications in PD patients, the choice of medication varies considerably between individuals. The most frequently prescribed medication for the treatment of PD is the use of drugs that boost the production of dopamine in the brain. Levodopa, which is modified by the brain enzyme to produce dopamine, is the most common medication for PD. Over the years, a number of drugs have been developed including dopamine agonists. However, the effectiveness of the drugs lessens after a period of treatment. Furthermore, some patients report side effects such as gastrointestinal ailments and psychological and cognitive problems (e.g. confusion, hallucinations, psychosis, etc).

Recent studies on the brains of PD patients have identified a loss of mitochondrial complex I function and generation of oxidative stress (Schapira, *Lancet Neurol.*, 7: 97-109 (2008)), which are thought to play a part in the progression of selective nigral dopaminergic degeneration in PD. The biochemical defects in PD patients resemble the findings in the animal model of MPTP (1-methyl-4-phenyl-1,2,3,6-tetrahydropyridine). MPP+ (1-methyl-4-phenylpyridinium), an active metabolite of MPTP, is a neurotoxin and has widely been used in in vitro experiments to cause parkinsonism. It is taken up through the dopamine transporter and accumulates in dopamine neurons. The absorbed MPP+ concentrates in the mitochondria and inhibits the activity of complex I of the electron transport chain resulting in the reduction of ATP generation and the production of reactive oxygen species (ROS), and consequently leads to selective dopaminergic neuronal death resulting in PD-like symptoms.

Several studies have reported to achieve parkinsonism in the human SH-SY5Y cell line using MPP+, thus generating a PD model for primary assessment of new therapeutic compounds (e.g., Kim et al., *Br. J. Nutr.*, 104: 8-16 (2010); Sun et al., *Eur. J. Pharmacol.*, 660: 283-90 (2011)). A simple cell-based PD model is more applicable for a preliminary screen of potential therapeutic candidates before clinical trials in mammals for the prevention and treatment of PD.

In addition to MPTP/MPP+, 6-hydroxydopamine (6-OHDA) is another chemical that has been broadly used to induce parkinsonism in experimental animals (Betarbet et al., *Bioessays*, 24: 308-18 (2002); Lane and Dunnett, *Psychopharmacology (Berl)*, 199: 303-12 (2008)). It enters the neurons via the dopamine and noradrenaline reuptake transporters and therefore often used in conjunction with a selective noradrenaline reuptake inhibitor (such as desipramine) to selectively kill dopaminergic neurons. It is considered to be an endogenous toxin since it was found in the urine of a PD patient (Andrew et al., *Neurochem. Res.*, 18: 1175-7 (1993)) and oxidation of dopamine can lead to the generation of 6-OHDA in vitro (Napolitano et al., *Chem. Res. Toxicol.*, 12: 1090-1097 (1999)). A wealth of evidence indicates that 6-OHDA generates reactive oxygen species and reduces the activities of glutathione and superoxide dismutase. Following intracerebral injection of 6-OHDA, striatal neurons begin to degenerate in 24 hr and striatal dopamine is depleted in 2-3 days.

N-methyl-D-aspartate (NMDA) receptors are ligand-gated ion channels located primarily within the central nervous system (CNS). They belong to the family of ionotropic glutamate receptors and are involved in neuronal communication and play important roles in synaptic plasticity and mechanisms that underlie learning and memory. Under normal conditions, NMDA receptors engage in synaptic transmission via the neurotransmitter glutamate, which regulates and refines synaptic growth and plasticity. However, when there are abnormally high levels of glutamate (i.e. under pathological conditions), NMDA receptors become over-activated, resulting in an excess of $Ca^{2+}$ influx into neuronal cells, which in turn causes excitotoxicity and the activation of several signaling pathways that trigger neuronal apoptosis. Glutamate-induced apoptosis in brain tissue also accompanies oxidative stress resulting in loss of ATP, loss of mitochondrial membrane potential, and the release of reactive oxygen species and reactive nitrogen species (e.g. $H_2O_2$, NO, $OONO^-$, $O_2^-$) causing associated cell damage and death. Decreased nerve cell function and neuronal cell death eventually occur.

Over-activation of the NMDA receptors is implicated in neurodegenerative diseases and other neuro-related conditions as it causes neuronal loss and cognitive impairment, and also plays a part in the final common pathway leading to neuronal injury in a variety of neurodegenerative disorders such as amyotrophic lateral sclerosis, Parkinson's disease, Alzheimer's disease and Huntington's disease, as well as conditions such as stroke. Recent findings have implicated NMDA receptors in many other neurological disorders, such as multiple sclerosis, cerebral palsy (periventricular leukomalacia), and spinal cord injury, as well as in chronic and severe mood disorders (Pogačić and Herrling, *Neurodegener. Dis.*, 6: 37-86 (2009)).

There remains a need for compounds and compositions that can protect neuronal cells from MPP+/6-OHDA and NMDA induced cell death, and/or inhibit the aggregation of α-synuclein, or which are otherwise useful for the treatment of neurodegenerative and neuropathological diseases such as Parkinson's disease or other diseases associated with α-synuclein aggregation.

BRIEF SUMMARY OF THE INVENTION

The present invention provides compounds and compositions, particularly pharmaceutical compositions, useful for treating neurodegenerative diseases or neuropathological conditions, including synucleinopathies, or for reducing aggregation of α-synuclein in a subject. Also provided are methods for using the compounds and compositions for the treatment of such diseases or conditions.

In one aspect, the present invention provides a composition, preferably a pharmaceutical composition, useful for treating a neurodegenerative disease or neuropathological condition in a subject, or for reducing aggregation of α-synuclein in a subject, the composition comprising *Alpinia officinarum* extract or a refined fraction thereof and, optionally, a pharmaceutically acceptable carrier or excipient.

In a related aspect, the invention provides a method of treating a neurodegenerative disease or neuropathological condition in a subject, or reducing aggregation of α-synuclein in a subject, the method comprising administering to the subject an effective amount of *Alpinia officinarum* extract or refined fraction thereof.

In another aspect, the invention provides a compound of Formula 1 for treating a neurodegenerative disease or neuropathological condition, or for reducing aggregation of α-synuclein:

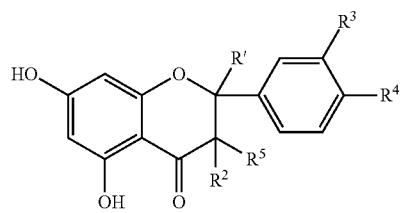

or a salt thereof, wherein R' is and $R^2$ are both H or together form a bond; and $R^3$, $R^4$, and $R^5$ are independently H, OH, or a $C_1$-$C_8$ alkoxy. Also provided is a pharmaceutical composition comprising one or more compounds of Formula 1 and a carrier or excipient, as well as a method of using such a compound or composition for the treatment of a neurodegenerative disease or neuropathological condition in a subject, or reducing aggregation of α-synuclein in a subject.

BRIEF DESCRIPTION OF THE SEVERAL VIEWS OF THE DRAWING(S)

Figure 5:
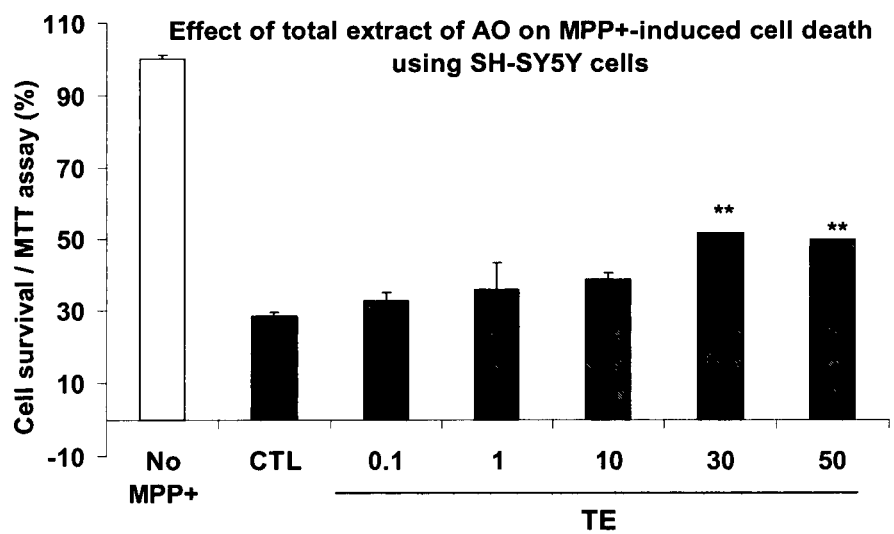

FIG. 5 is a graph depicting survival rate of SH-SY5Y cells pretreated with various concentrations of total AO extract (TE, μg/mL) for 2 hr followed by co-treatment with MPP+ (50 μM). Data are presented in % survival as compared to control without MPP+ treatment (set as 100% survival), and statistical analysis was performed in comparison to DMSO-treated control (Student T-test), wherein *=P<0.05, **=P<0.005.

Figure 6:
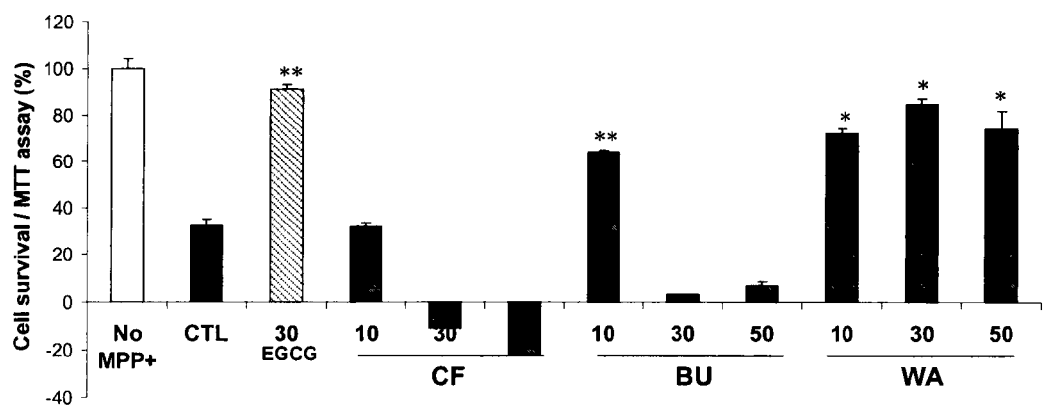

FIG. 6 is a graph depicting survival of SH-SY5Y cells pretreated with various concentrations of chloroform (CF), butanol (BU) and water (WA) fractions of the AO extract (μg/mL) for 2 hr followed by co-treatment with MPP+ (50 μM). Data are presented in % survival as compared to control without MPP+ treatment (set as 100% survival), and statistical analysis was performed in comparison to DMSO-treated control (Student T-test), wherein *=P<0.05, **=P<0.005.

Figure 7:
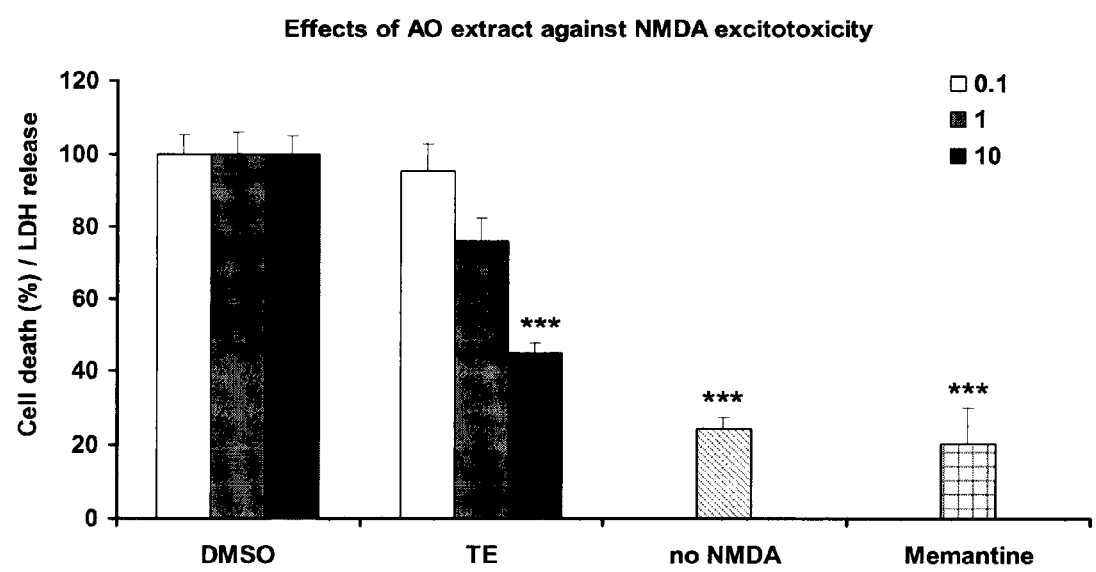

FIG. 7 is a graph depicting cell death of primary neurons pretreated with total AO extract (TE, μg/mL) for 2 hr prior to co-treatment with NMDA for 20 min, expressed as a percent of vehicle (DMSO)-treated control using one-way ANOVA. ***=P<0.005. Memantine (10 μM) was used as positive control.

Figure 8:
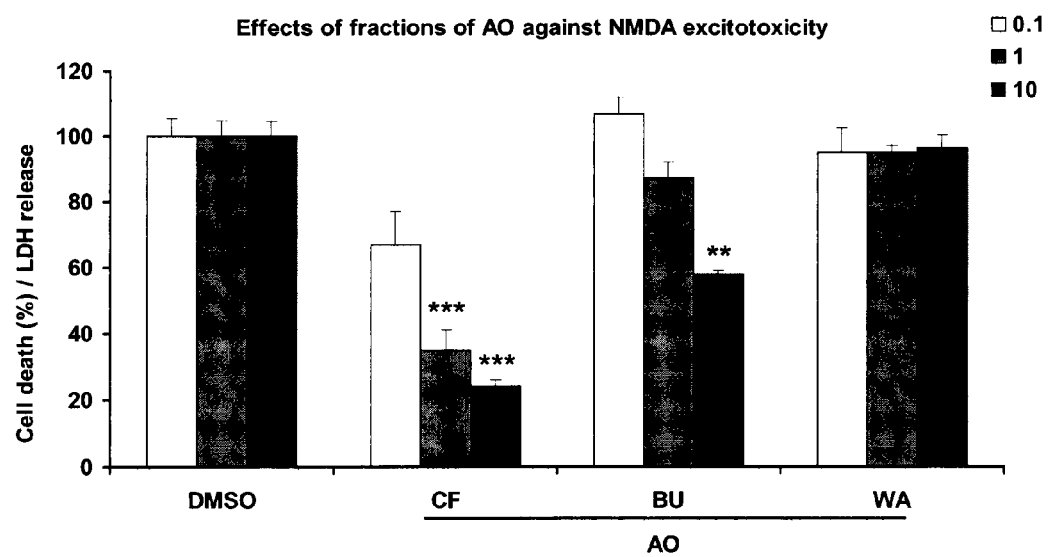

FIG. 8 is a graph depicting cell death of primary neurons pretreated with chloroform (CF), butanol (BU) and water (WA) subfractions of the total AO extract (μg/mL) for 2 hr prior to co-treatment with NMDA for 20 min, expressed as a percent of vehicle (DMSO)-treated control using one-way ANOVA. ***=P<0.005. Memantine (10 μM) was used as positive control.

Figure 9:
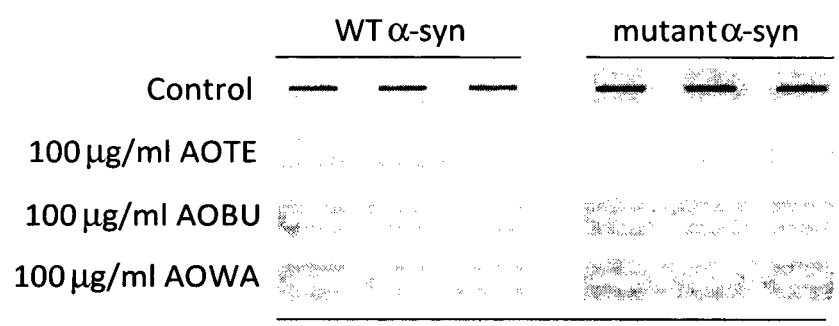

FIG. 9 is a Western Blot of α-synuclein from the lysates of SH-SY5Y cells transfected with WT-α-syn or mutant α-syn and treated with 100 μg/mL total AO extract (AOTE), butanol fraction (AOBU), or water fraction (AOWA).

Figure 10:
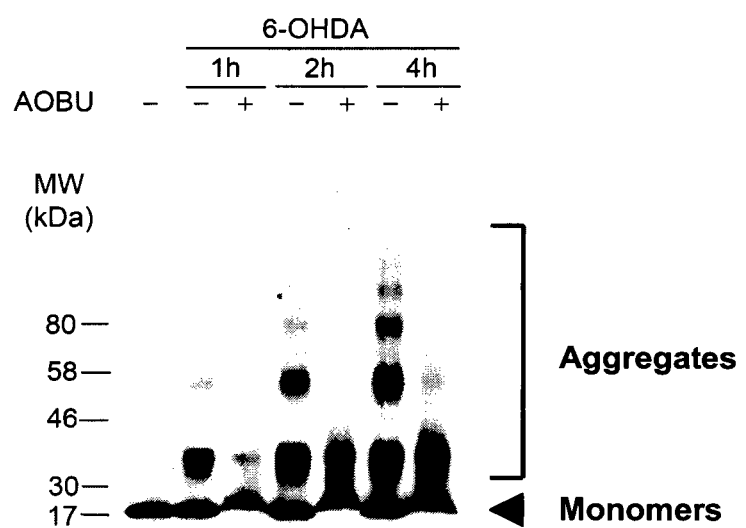

FIG. 10 is a Western Blot of α-synuclein (1 μg) following incubation with 6-OHDA (50 μg) with or without butanol fraction of *Alpinia officinarum* extract (AOBU) (320 μg) for 1-4 hr at 37° C.

Figure 11:
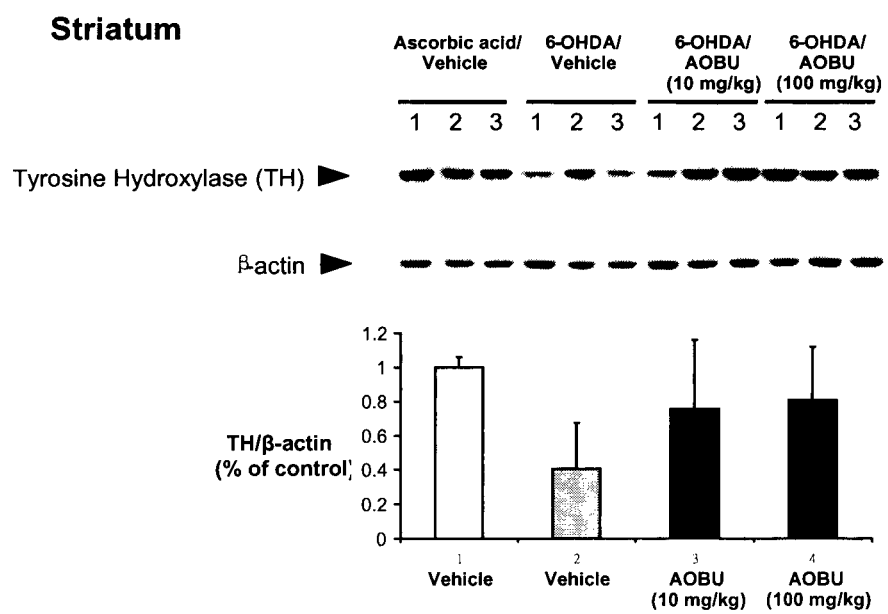

FIG. 11 depicts Western Blot analysis for TH levels in the striata of mice treated with 6-OHDA and the butanol fraction of *Alpinia officinarum* extract (AOBU).

Figure 12:
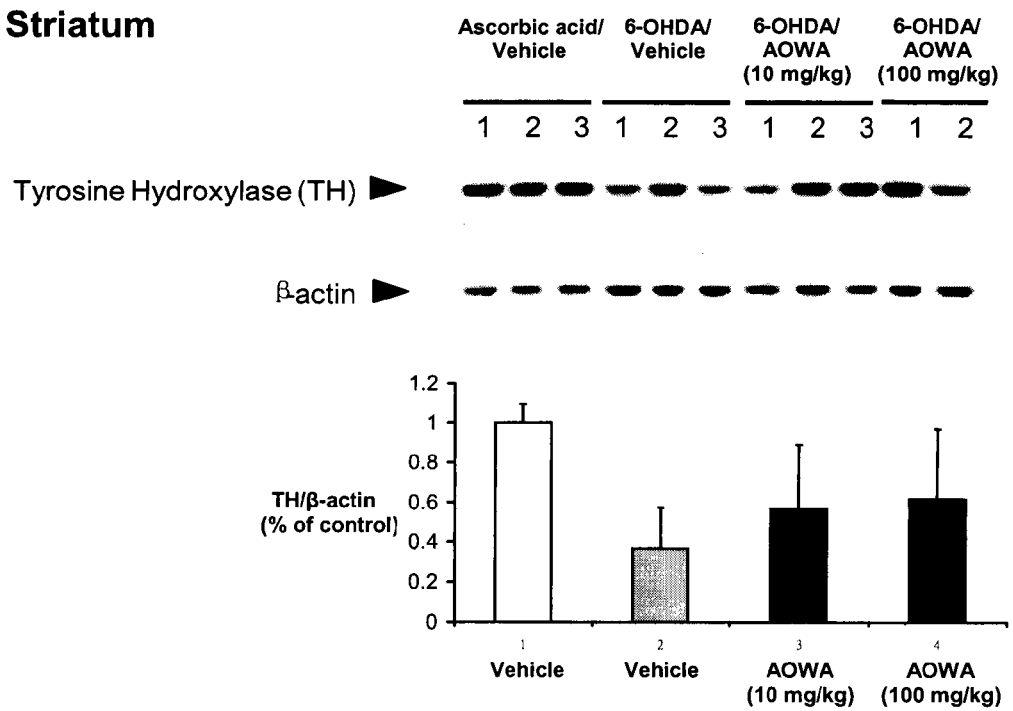

FIG. 12 depicts Western Blot analysis of TH levels in the striata of mice treated with 6-OHDA and the water fraction of *Alpinia officinarum* extract (AOWA).

Figure 13:
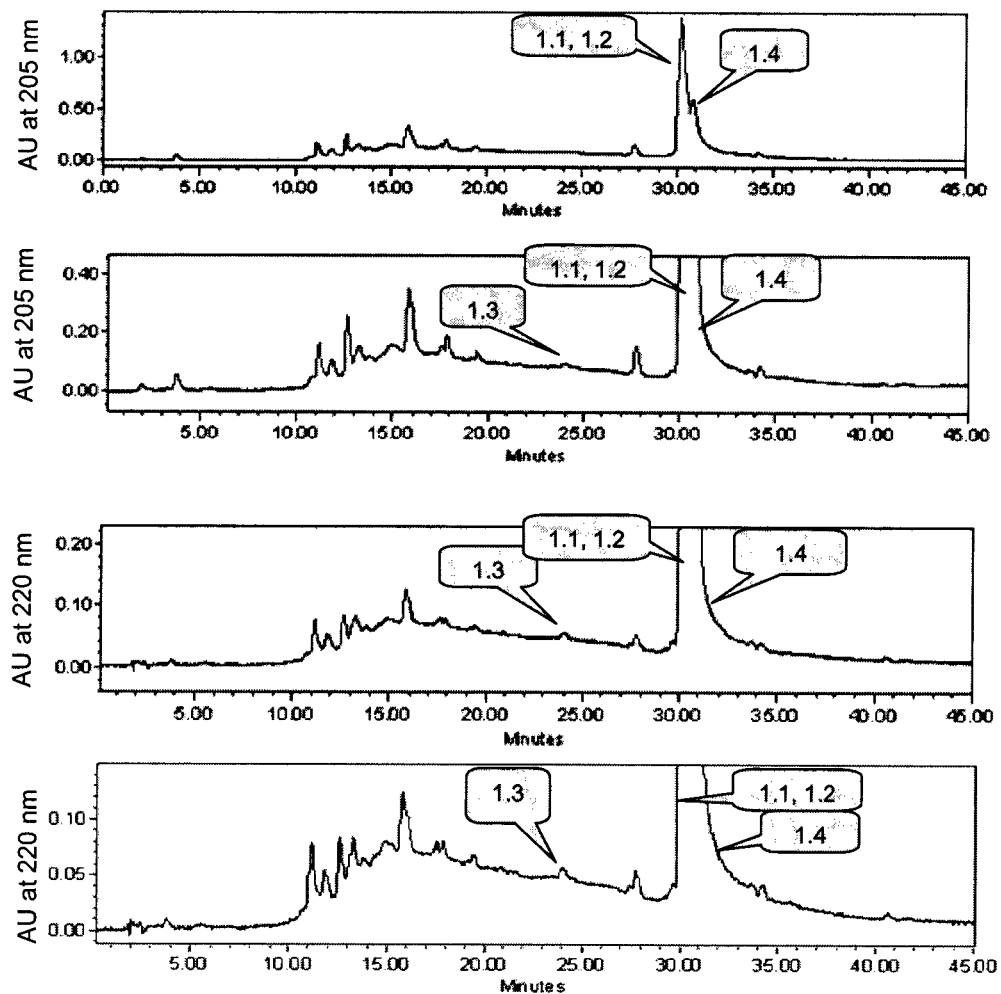

FIG. 13 shows HPLC chromatograms of the butanol fraction of *Alpinia officinarum* extract (AOBU).

Figure 14:
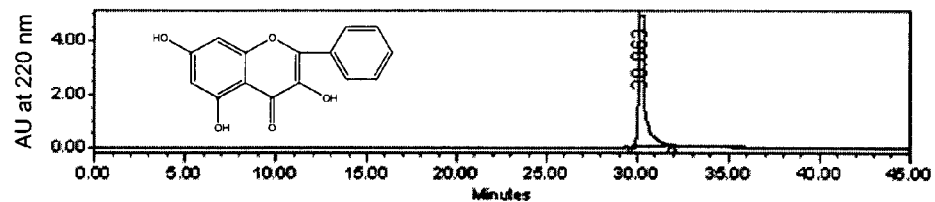
Figure 14:
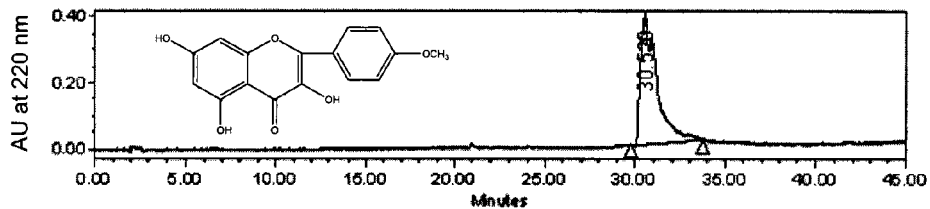
Figure 14:
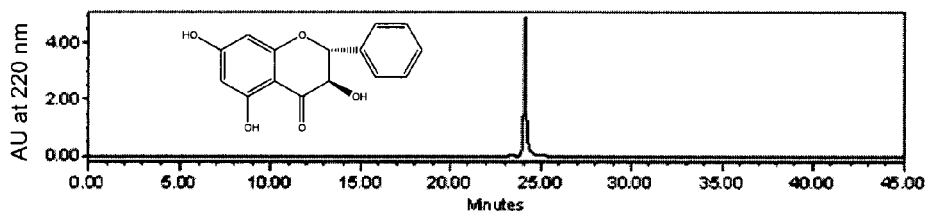
Figure 14:
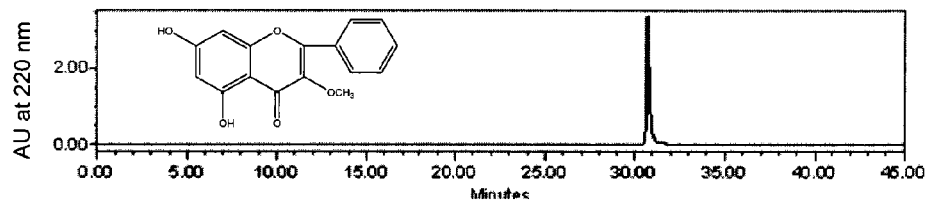

FIG. 14 shows the structure of four compounds found in the butanol fraction of *Alpinia officinarum* extract (AOBU).

DETAILED DESCRIPTION OF THE INVENTION

In one aspect, the present invention provides a composition, preferably a pharmaceutical composition, useful for treating a neurodegenerative disease or neuropathological condition in a subject, or for reducing aggregation of α-synuclein in a subject, the composition comprising *Alpinia officinarum* (AO) extract or a refined fraction thereof. *Alpinia officinarum* is an herbal species of *Alpinia* in the ginger family (Zingiberaceae) often found in southern China and used in traditional Chinese medicine.

*Alpinia officinarum* extract can comprise, consist essentially of, or consist of any solvent-soluble portion of the plant *Alpinia officinarum*. The extract can comprise a hydrophilic portion of *Alpinia officinarum*, such as, for example a water-soluble portion of the plant. Alternatively, or in addition, the extract can comprise a lipophilic portion of *Alpinia officinarum*, such as, for example, a portion soluble in oil or other non-polar organic solvent like toluene or chloroform. Also, or instead, the extract can comprise an amphiphilic portion, (e.g., portion soluble in both polar and non-polar solvents to at least some measurable degree). Furthermore, the extract can comprise, consist essentially of, or consist of any refined fraction of one or more of the hydrophilic, lipophilic, or amphiphilic portions. The extract can comprise any of the foregoing portions alone or in any combination.

According to one aspect of the invention, the extract comprises, consists essentially of, or consists of an alcohol-soluble portion of *Alpinia officinarum*, for instance, that portion having a solubility in 100% methanol of about 10 mg/mL or more (e.g., about 15 mg/mL or more, about 20 mg/mL or more, about 25 mg/mL or more, about 30 mg/mL or more, about 35 mg/mL or more, or about 40 mg/mL or more). Alternatively, or in addition, the extract comprises, consists essentially of, or consists of a portion of *Alpinia officinarum* having a solubility in 70% methanol/water (v/v) of about 10 mg/mL or more (e.g., about 15 mg/mL or more, about 20 mg/mL or more, about 25 mg/mL or more, about 30 mg/mL or more, about 35 mg/mL or more, or about 40 mg/mL or more).

In one embodiment, the extract comprises, consists essentially of, or consists of an alcohol-soluble (e.g, butanol-soluble) portion of *Alpinia officinarum*, which portion comprises one or more, two or more, three or more, or all four of compounds 1.1, 1.2, 1.3, and 1.4 of Table 1, below. In a more particular embodiment, the extract comprises about 100-200 mg (e.g., about 150 mg) of compound 1.1 per gram of extract, about 50-100 mg (e.g., about 60 mg) of compound 1.2 per gram of extract, about 1-5 mg (e.g., about 2 mg) of compound 1.3 per gram of extract, and/or about 5-20 mg (e.g., about 10 mg) of compound 1.4 per gram of extract, or other amounts of compounds 1.1-1.4 in an equivalent weight ratio.

The extract can be prepared by any suitable technique, for instance, by extracting the desired portions of *Alpinia officinarum* with a suitable solvent. Examples of suitable solvents include water, water-miscible solvents such as alcohols (e.g., ethanol, methanol, butanol, and the like), and polar organic solvents (e.g., toluene, acetone, chloroform, and the like). Suitable extraction techniques are described in the Examples set forth herein, although the described techniques are in no way intended to limit the scope of the invention.

Further refinement of the extracted portion can be performed by any suitable technique, such as by further extraction with the same or a different solvent, or by other purification or fractionation technique. Some such techniques are described in the Examples.

The extract can be isolated from the solvent, if desired, by evaporating or otherwise separating the extract from the solvent. Furthermore, the extract or refined fraction thereof can be used alone or in combination with a solvent or other carrier or excipient, preferably a pharmaceutically acceptable carrier or excipient.

The extract or refined portion or fraction thereof can be used as part of a composition (e.g., comprising a carrier, diluent, excipient or other appropriate components) in any concentration. Desirably, the composition will comprise about 1 μg/mL or more (e.g., about 5 μg/mL or more, about 10 μg/mL or more, about 15 μg/mL or more, or about 20 μg/mL or more) of the extract or refined portion thereof. In some embodiments, the composition will contain higher concentrations of the extract or refined portion thereof such as about 25 μg/mL or more (e.g., about 30 μg/mL or more, about 35 μg/mL or more, about 40 μg/mL or more, or about 45 μg/mL or more), about 50 μg/mL or more (e.g., about 55 μg/mL or more, about 60 μg/mL or more, about 65 μg/mL or more, or about 70 μg/mL or more), or even about 75 μg/mL or more (e.g., about 80 μg/mL or more, about 85 μg/mL or more, about 90 μg/mL or more, about 95 μg/mL or more, or about 100 μg/mL or more).

In another aspect, the invention provides a compound of Formula 1 and use thereof for the treatment of a neurodegenerative disease or neuropathological condition in a subject, or for reducing aggregation of α-synuclein in a subject:

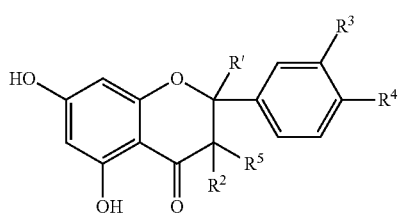

1 or a salt thereof, wherein $R^1$ and $R^2$ are both H or together form a bond; and $R^3$, $R^4$, and $R^5$ are independently H, OH, or a $C_1$-$C_8$ alkoxy (e.g., a $C_1$-$C_6$ alkoxy or $C_1$-$C_3$ alkoxy, such as methoxy or ethoxy). In some embodiments, $R^3$ is H and/or $R^4$ is H or $C_1$-$C_8$ alkoxy, such as a $C_1$-$C_6$ alkoxy or $C_1$-$C_3$ alkoxy (e.g., methoxy or ethoxy). Alternatively, or in addition, $R^5$ is hydroxyl or $C_1$-$C_8$ alkoxy, such as a $C_1$-$C_6$ alkoxy or $C_1$-$C_3$ alkoxy (e.g., methoxy or ethoxy). Examples of such compounds include, without limitation, any of compounds 1.1 to 1.4 and salts thereof:

| Compound | Structure |
|---|---|
| 1.1 | 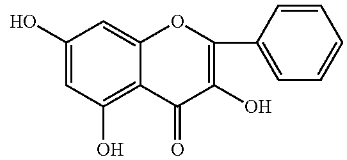 [SMILES: O=c1c(O)c(-c2ccccc2)oc2cc(O)cc(O)c12] |
| 1.2 | 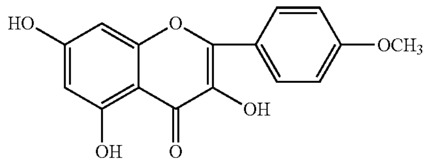 [SMILES: COc1ccc(-c2oc3cc(O)cc(O)c3c(=O)c2O)cc1] |
| 1.3 | 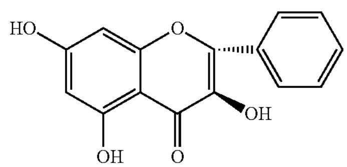 |
| 1.4 | 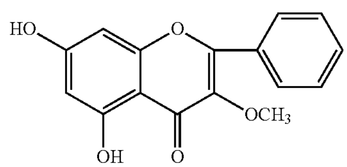 [SMILES: COc1c(-c2ccccc2)oc2cc(O)cc(O)c2c1=O] |

The compound of Formula 1 can be provided by any suitable technique. For instance, the compounds can be synthesized using routine methods, or the compounds can be extracted from a natural source such as *Alpinia officinarum*, as illustrated in the Examples provided herein.

Salts of non-salt compounds of Formula 1 can be prepared using relatively nontoxic acids or bases, depending on the particular starting "parent" compound. Base addition salts of parent compounds with relatively acidic functionalities can be prepared by contacting the free acid form of such compounds with a sufficient amount of the desired base, either neat or in a suitable inert solvent. Examples of pharmaceutically acceptable base addition salts include sodium, potassium, calcium, ammonium, organic amino, magnesium salts, and the like. Acid addition salts of parent compounds having relatively basic functionalities can be obtained by contacting the free base form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogen-carbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like.

The compound of Formula 1 can be part of a composition comprising one or more (e.g., two or more, three or more, four or more, etc.) different compounds of Formula 1. By way of illustration, the composition can comprise one or more, two or more, three or more, or all four of compounds 1.1-1.4 (Table 1). In one embodiment, the composition comprises about 100-200 mg (e.g., about 150 mg) of compound 1.1 per gram of composition, about 50-100 mg (e.g., about 60 mg) of compound 1.2 per gram of composition, about 1-5 mg (e.g., about 2 mg) of compound 1.3 per gram of composition, and/or about 5-20 mg (e.g., about 10 mg) of compound 1.4 per gram of composition, or other amounts of compounds 1.1-1.4 in an equivalent weight ratio.

Although the one or more compounds of Formula 1 or composition comprising the same is not limited by any particular degree of purity, in some embodiments the one or more compounds of Formula 1 have a relatively high level of purity. For instance, the one or more compounds of Formula 1 can have a purity of about 80% or more, about 85% or more, about 90% or more, or about 99% or more.

The compounds of Formula 1 can be used in any effective amount. In some embodiments, the one or more compounds of Formula 1 (individually or collectively) are used at a concentration of about 0.2 µM or more (e.g., about 0.5 µM or more or about 0.8 µM or more), such as about 1 µM or more (e.g., about 2 µM or more, about 5 µM or more, or about 8 µM or more), or even about 10 µM or more (e.g., about 12 µM or more, about 15 µM or more or about 20 µM or more).

Compositions comprising an extract of *Alpinia officinarum*, a refined fraction thereof, or one or more compounds of Formula 1, as described above, can further comprise other active components. For instance, the compositions can comprise other active agents isolated from *Alpinia officinarum*, or other agents known in the art to be useful for the treatment of neurodegenerative or neuropathological conditions.

The composition comprising an extract of *Alpinia officinarum*, a refined fraction thereof, or one or more compounds of Formula 1, as described above, also can comprise any suitable carrier or excipient, desirably a pharmaceutically acceptable carrier or excipient. The carriers or excipients can be any of those conventionally used and is limited only by physico-chemical considerations, such as solubility and lack of reactivity with the active compound(s), and by the route of administration. According to one embodiment, the composition comprises a cyclodextrin.

There are a variety of suitable formulations for the pharmaceutical composition of the present inventive methods, for instance, oral, aerosol, or parenteral (e.g., subcutaneous, intravenous, intra-arterial, intramuscular, or intraperitoneal) formulations. Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds and compositions of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds and compositions of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Alternatively, the compounds and compositions described herein can be modified into a depot form, such that the manner in which the compound of the invention is released into the body to which it is administered is controlled with respect to time and location within the body. Depot forms of compounds and compositions can be, for example, an implantable composition comprising the compound and a porous material, such as a polymer, wherein the compound is encapsulated by or diffused throughout the porous material. The depot is then implanted into the desired location within the body and the compound is released from the implant at a predetermined rate by diffusing through the porous material.

In some contexts, the compounds and compositions of the invention can be advantageously administered via an implanted pump that allows intrathecal delivery. Such a delivery method is especially useful for delivery of drugs to the CNS when the drugs administered do not otherwise sufficiently penetrate the blood-brain barrier.

The compounds and compositions described herein are believed to be especially useful for treating a neurodegenerative disease or neuropathological condition in a subject. In this respect, the invention provides a method for treating such diseases, the method comprising administering to the subject a therapeutically effective amount of the compound or composition.

Without wishing to be bound by any particular theory or mechanism of action, it is believed that the compounds and compositions described herein are able to exert a therapeutic effect towards neurodegenerative disease or neuropathological conditions, at least in part, by inhibiting the aggregation of α-synuclein and/or deposition of insoluble aggregates of α-synuclein in cells or in tissues, particularly in neurons, glial cells, or tissues comprising such cells. Thus, in another aspect, the invention provides a method of inhibiting the aggregation activities of α-synuclein, including the aggregation of α-synuclein and/or deposition of insoluble aggregates of α-synuclein, in cells or in tissues, particularly in neurons, glial cells, or tissues comprising such cells. The method comprises contacting α-synuclein protein with a compound or composition of the invention as described herein. The α-synuclein protein can be contacted with the compound or composition by any suitable method, such as by administering the compound or composition to cells or tissues containing the protein (e.g., neurons or glial cells) in vitro or in vivo. When the cells or tissues are in vivo, administering the compound or composition to the cells or tissues can be accomplished by administering the compound or composition to a subject that comprises the cells or tissues.

The method of inhibiting the aggregation activities of α-synuclein protein can be performed with any cell or tissue that contains the protein, particularly cells or tissues that exhibit α-synuclein aggregation or deposition (i.e., α-synuclein plaque formation). Such cells and tissues include, for instance, the cells of a subject afflicted with a disorder characterized by abnormal α-synuclein aggregation activities, such as the aggregation of α-synuclein and/or deposition of insoluble aggregates of α-synuclein, typically to a degree sufficient to cause a pathological effect and in which inhibition of α-synuclein aggregation activities could prevent, inhibit or ameliorate the pathology or symptomology of the disease. Such disorders are known as synucleinopathies.

Thus, in a related aspect, the compounds and compositions provided herein can be used in a method of treating synucleinopathies. The method comprises administering to a subject the compound or composition.

More specifically, non-limiting examples of neurodegenerative diseases and neuropathological conditions include, without limitation, acute and chronic disorders of the CNS, ranging from neuropathological conditions such as neuropathic pain, stroke, brain trauma, and epilepsy to neurodegenerative diseases such as amyotrophic lateral sclerosis, Alzheimer's disease, Parkinson's disease and Huntington's disease. Non-limiting examples of synucleinopathies, many or all of which also might be considered neurodegenerative diseases or neuropathological conditions, include Parkinson's disease (PD), dementia with Lewy bodies (DLB), pure autonomic failure (PAF), multiple system atrophy (MSA), Lewy body variant of Alzheimer's disease (AD), Hallervorden-Spatz disease, pantothenate kinase associated neurodegeneration (PKAN), and neurodegeneration with brain iron accumulation type 1 (NBIA1).

For the purposes described herein, inhibition of α-synuclein aggregation or inhibition of the deposit of insoluble α-synuclein aggregates includes a reduction in such activity by any degree, including partial and total inhibition. Thus, for instance, if the aggregation or deposition of α-synuclein protein is reduced, by any degree, in the presence of a compound or composition of the invention as compared to the level of aggregation or deposition of α-synuclein in the absence of the compound or composition, such aggregation or deposition of α-synuclein is considered to be inhibited. Desirably, the aggregation or deposition of α-synuclein is inhibited to an extent sufficient to ameliorate to any degree or to eliminate a pathological state or some symptom thereof.

Similarly, a disease or pathological condition is considered to be treated in the context of the invention if any symptom or other characterizing feature of the disease or condition is ameliorated or eliminated by any amount. Thus, for instance, a reduction in the degree or rate of neurodegeneration in a subject to which a compound or composition of the invention has been administered as compared to the same subject or similar subject in the absence of such administration is considered to be an indication that the disease or disorder has been treated to some degree. Similarly, any reduction in a biomarker of the disease (e.g., α-synuclein aggregation or plaque formation) in a subject is an indication that the disease or disorder has been treated to some degree.

The methods described herein can be performed with respect to any type of host, such as an animal, preferably a mammal or a human. For instance, the host can be a person afflicted with any of the diseases or conditions discussed herein.

In a related aspect, the compounds and compositions can be used in a method of manufacturing a medicament useful for the treatment of any of the foregoing diseases or disorders.

The following examples further illustrate the invention but, of course, should not be construed as in any way limiting its scope.

EXAMPLES

MATERIALS AND METHODS: The following materials and methods were used throughout the Examples except as otherwise noted.

*Alpinia officinarum*

The first batch of the rhizome of *Alpinia officinarum* Hance (Zingiberaceae) (AO) was cultivated in Guangdong province, China and purchased from Sichuan Medicinal Herb Ltd. (Chengdu, China) in August, 2000. The second batch of AO was harvested at Longtang, Xuwen County, Guangdong Province, China, in August 2009.

Preparation of the Total Extract:

The rhizome of *Alpinia officinarum* Hance (200 g) was first dried and immersed in 1.5 L 70% ethanol (material to solvent ratio at 1 to 5-10) for 30 min. The herb-solvent mixture was then refluxed 3 times for 2 hr each. The extract was filtered and the filtrate was evaporated to dryness to give 18 g of the total extract (TE).

The air-dried rhizome of *Alpinia officinarum* Hance (8.0 kg) was first dried and immersed in 40 L 70% ethanol (material to solvent ratio at 1 to 8) for 30 min. The herb-solvent mixture was then refluxed 3 times for 2 hr each. The extract was filtered and the filtrate was evaporated to dryness to give 700 g of the total extract (TE).

Preparation of Refined Fractions (CF, BU, WA, BU2, BU3, WA2, BU2-2, BU2-3, BU3-3):

The total extract (TE, 6.6 g) was dissolved/suspended in water (weight and water ratio at 1:5-10) and sequentially extracted with chloroform (CF) and water-saturated butanol (BU) at 1 to 1 volume ratio. Extraction with each different solvent was repeated 3 times and the solvent extracts were filtered and dried to give fractions CF (3.0 g), BU (1.5 g), and water (WA, 1.9 g). 500 mg of BU was dissolved in 1 mL MeOH and added dropwise to a 50 mL flask containing 1.2 g silica gel. The sample was air-dried at room temperature and then added to a silica gel column (30 g silica gel, column diameter 3 cm and volume 50 mL). The column was eluted with 250 mL of 5% methanol and dichloromethane (MeOH/DCM) initially, followed by 200 mL of 15% MeOH/DCM, and finally 200 ml MeOH/DCM/$H_2O$ (1:1:0.1). A total of 41 subfractions were collected, combined based on TLC results, and dried under vacuum to give three subfractions including BU1 (178 mg), BU2 (50 mg), and BU3 (135 mg). BU3 was subsequently dissolved in methanol and mixed with silica gel (Merck 70-200 mesh) at the ratio of sample to silica gel 1:3. A column with silica gel at the amount of 5-10 times of the sample was packed and a gradient system of chloroform, methanol, and water at varying ratios (i.e., $CHCl_3$/MeOH (1:1), $CHCl_3$/MeOH (3:7), $CHCl_3$/MeOH/$H_2O$ (60:40:0.1)), was used for column elution. For each solvent condition, the volume used was in the range of 2 to 5 times of the column volume. The subfractions were collected, combined based on TLC, and dried under vacuum to give BU3-1, BU3-2, and BU3-3. Water extract (WA, 1.9 g) was dissolved in 6 mL water, and then was subjected to macroporous resin D101 column chromatography (60 g, D101 column diameter 4 cm and volume 120 mL), eluting with water, 50%, 96% ethanol. The eluted solvent was concentrated under vacuum to afford three subfractions including WA1 (0.80 g), WA2 (0.90 g) and WA3 (0.15 g).

The total extract (TE, 700 g) was dissolved/suspended in 1500 mL water and sequentially extracted with chloroform (CF) and water-saturated butanol (BU) at 1 to 1 volume ratio. Extraction with each different solvent was repeated 5 times and the solvent extracts were filtered and dried to give fractions CF (120 g), BU (150 g), and water (WA, 400 g).

A part of fraction BU (18.0 g) was dissolved in 18 mL MeOH and added dropwise to a 250 mL flask containing 18.0 g silica gel. The sample was air-dried at room temperature and then subjected to silica gel column chromatography (360 g silica gel, column diameter 5 cm and volume 800 mL) using a stepwise gradient elution of dichloromethane, methanol and water at ratios of 19:1:0 (2000 mL), 17:3:0 (1.6 L) and 10:10:1 (1.6 L) to afford three fractions including Bin (5.5 g), BU2 (3.8 g) and BU3 (7.3 g). BU2 (2.0 g) was further chromatographed over silica gel column, eluted with chloroform and methanol using a stepwise gradient with a ratio of 20:1 (800 mL), 10:1 (800 mL) and 5:1 (800 mL) to give BU2-1 (400 mg), BU2-2 (1010 mg) and BU2-3 (500 mg). A part of BU3 (5.0 g) was subsequently dissolved in 8.0 mL methanol and mixed with silica gel (Merck 70-200 mesh) at the ratio of sample to silica gel 1:1, and then the mixed BU3 was further chromatographed over silica gel column (200 g silica gel, column diameter 5 cm and volume 400 mL), and eluted with a gradient system of chloroform, methanol, and water at varying ratios (i.e., $CHCl_3$/MeOH (1:1, 1000 mL), $CHCl_3$/MeOH (3:7, 1000 mL), $CHCl_3$/MeOH/$H_2O$ (60:40:0.1, 1000 mL)). The subfractions were collected, combined based on TLC behavior, and dried under vacuum to give BU3-1 (1.2 g), BU3-2 (2.6 g), and BU3-3 (1.1 g).

WA extract (250 g) was further subjected to macroporous resin D101 column (2.5 Kg) chromatography, eluted with water (52 L), 50% (18 L) and 95% ethanol (11 L) for further fractionation. Three subfractions were fractionated from the WA extract: WA1 (water eluted, 100 g), WA2 (50% ethanol eluted, 120 g), and WA3 (95% ethanol eluted, 11.5 g).

α-Synuclein Aggregation Assay:

Recombinant α-synuclein (7 µg) was incubated with samples in 1×Tris-Buffered Saline, (1×TBS: 20 mM Tris, pH 7.5; 500 mM NaCl, pH 7.5 with HCl) at room temperature for 7 days. After incubation, the samples were filtered with a Bio-Dot SF Microfiltration Apparatus (Bio Rad) according to the manufacturer's instructions. After filtration, the amount of trapped α-synuclein was determined by Western Blot analysis with anti-α-synuclein antibodies.

Recombinant α-synuclein Aggregation Assay with the Presence of 6-OHDA:

Recombinant human α-synuclein (1 µg) were incubated with 6-OHDA (50 µg) with or without AOBU (320 µg) for 1-4 hr at 37° C. without shaking. The samples were then mixed with 1×SDS buffer and boiled at 100° C. for 5 min. The proteins samples were resolved in 8% polyacrylamide gel, and transferred onto nitrocellulose membranes. Western blot analysis was performed with an anti-α-synuclein monoclonal antibody (BD Transduction). An equal amount of protein was loaded in each lane.

SH-SY5Y Culture and Survival Assay Against MPP+ (1-methyl-4-phenylpyridinium) Insult:

SH-SY5Y cell line, a human neuroblastoma cell line (obtained from ATCC) that expresses tyrosine hydroxylase and dopamine transporter activities, was maintained in MEM containing 10% fetal bovine serum. Cells were plated onto 48-well plates (NUNC) at a density of $1 \times 10^5$ cells per well overnight. SH-SY5Y cells were pretreated with AO total extract and fractions for 2 hr prior to MPP+ treatment. 30 µM epigallocatechin gallate (EGCG; Sigma) was used as a positive control. Following 2 hr pretreatment, cells were co-treated with AO samples and 50 µM MPP+ for 72 hr. Cell survival was assayed and quantified using a colorimetric MTT (3-(4,5-dimethylthiazol-2-yl)-2,5-diphenyltetrazolium bromide) assay (USB Corporation).

Neuronal Cultures and Neuron Survival Assay Against NMDA (N-methyl-D-Aspartate) Insult:

Primary cortical neurons were prepared from embryonic day 18 (E18) Sprague-Dawley rats. Neurons were plated onto 48-well plates (NUNC) at a density of $1.1 \times 10^5$ cells per well using Neurobasal medium (Invitrogen) supplemented with 2% B27 (Invitrogen). Neurons at 11-12 days in vitro (DIV) were subjected to AO extract and fractions for 2 hr prior to NMDA treatment. 10 µM memantine (Sigma) was used as the positive control. After drug treatment, the neurons were rinsed with Locke's solution (5 mM potassium chloride, 128 mM sodium chloride, 2.7 mM calcium chloride, 1 mM di-sodium hydrogen orthophosphate, 5 mM HEPES and 10 mM glucose in Milli-Q water), and incubated with Locke's plus glycine (10 µM) for another 15 minutes. After incubation, the neurons were co-treated with AO extract or fractions (dissolved in Locke's plus glycine solution) and NMDA (20 µM; Sigma) for 20 minutes. The amount of neuronal injury was assayed and quantified using the lactate dehydrogenase release assay (Roche).

6-OHDA Injected Mouse PD Model

6-OHDA (50 µg, Sigma) or the same volume of the vehicle (L-ascorbic acid; Sigma) was injected into the cerebral ventricles of male C57B/6 mice (10-12-week-old). Desipramine (25 mg/kg) was intraperitoneally administered 1 hr before the injection of 6-OHDA to block noradrenaline reuptake to protect neurons other than dopaminergic neurons. Mice were anaesthetized using chloral hydrate (400 mg/kg, i.p.) and placed into a stereotaxic frame adaptor for mice. 6-OHDA was dissolved at a concentration of 10 µg/µL in saline containing 0.2% ascorbic acid and 5 µL was injected at a rate of 0.5 µL/min. The needle (Hamilton) was left in place for 7 min after the injection before retraction. The injection was performed using the following co-ordinates: 0.5 mm anteroposterior and 1.0 mm mediolateral from bregma, 2.0 mm dorsoventral from skull.

Biochemical Fractionation of Animal Brain Tissues

Different parts of brain tissues were dissected, weighed, and homogenized in 3 mL/g of Triton X-100 buffer (10 mM Tris-HCl [pH 7.6], 150 mM NaCl, 1% Triton X-100 and protease inhibitors). The supernatant, after centrifugation at 15,000×g at 4° C. for 0.5 hr, was labeled as "Triton soluble fraction". The pellet was re-extracted with 1 mL/g of 0.1% SDS buffer (10 mM Tris-HCl [pH 8.0], 150 mM NaCl, 1% Triton X-100, 0.5% sodium deoxycholate and 0.1% SDS) and fractionated by centrifugation at 15,000×g at 4° C. for 0.5 hr, and the supernatant was labeled as "SDS-soluble fraction". The pellet was resuspended, dissolved and boiled in 3% SDS containing 5% β-mercaptoethanol (1 mL/g pellet), and the lysate was termed "SDS-insoluble fraction". Proportional amounts to the original brain weight were loaded on separate lanes and transferred to nitrocellulose membrane. The membrane was incubated with antibodies to tyrosine hydroxylase (TH, 1:4000, Millipore) and β-actin (1:2000, Sigma). Blots were then incubated with HRP-conjugated secondary antibody (1:4000, Cell signaling technology), followed by chemiluminescent detection (ECL; Amersham).

Determination of Compound Composition in Fraction AOBU

HPLC conditions: A HPLC-DAD method has been developed for the analysis of and quality control of AOBU and standard compounds. A waters HPLC system consisting of a 600 pump, a 717 auto-sampler and a UV/VIS Photodiode Array 2996 Detector was used for all of the analysis. Chromatographic separations were carried out on a SunFire C18 column (Particle size 5 µm, 4.6 mm×150.0 mm) with acetonitrile (as Solvent A) and water (as Solvent B) in the mobile phase at a flow rate of 1.0 mL/min at room temperature. A gradient elution was applied from 10% to 85% of solvent A starting from 0 to 48 min (0-40 min 10%~85% ACN; 40-45 min, 85% ACN; 45-48 min, 85%~10% ACN). Samples were dissolved in MeOH and filtered through a 0.45 µm Millipore syringe filter unit. Twenty microliter samples were injected for HPLC analysis.

Example 1

The following example illustrates the use of *Alpinia officinarum* extract to inhibit α-synuclein aggregation.

Total extract (TE) of *Alpinia officinarum* (AO) was prepared as described in Material and Methods. Purified GST-α-synuclein in TBS was then incubated with the extract (10 or 50 μg) for 7 days at room temperature. After incubation, the samples were filtered with a Bio-Dot SF microfiltration apparatus (Bio Rad) according to the manufacturer's instructions. After filtration, the amount of trapped α-synuclein was determined by Western blot analysis. The assay was performed in triplicate, and the results are provided in FIG. 1.

Figure 1:
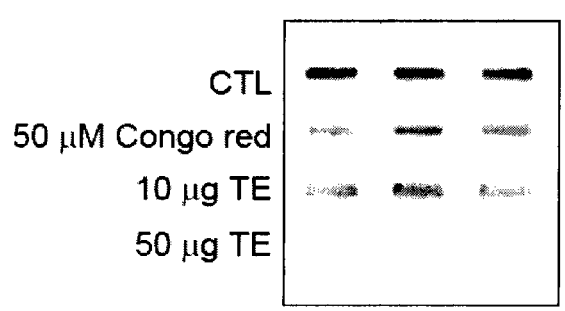
FIGS. 1A and 1B depict the results of a Western Blot Analysis (FIG. 1A) and quantitative analysis of band intensity (FIG. 1B) of α-synuclein (7 μg) incubated with total extract of *Alpinia officinarum* (AOTE, 10 or 50 μg) for 7 days.
Figure 1:
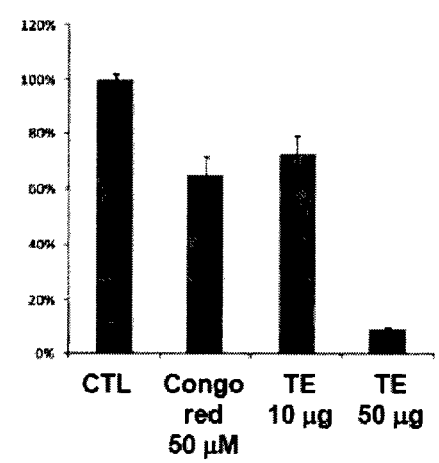

As seen in FIG. 1, TE strongly inhibits α-synuclein aggregation when compared to vehicle-treated control. Furthermore, the anti-aggregation activity of the total extract (TE) of *Alpinia officinarum* (AO) is dose-dependent and it is more potent than the well-studied anti-aggregation compound, Congo red (FIG. 1).

Example 2

The following example illustrates the use of a butanol and water fraction of *Alpinia officinarum* to inhibit α-synuclein aggregation.

To identify the active anti-aggregation components in AO, the total extract of AO was further fractionated using chloroform (CF), butanol (BU), and water (WA). Each fraction (50 μg) was incubated with α-synuclein (7 μg) recombinant protein for 7 days. The assay was performed in triplicate and repeated at least 2 times. Protein was detected as described in Example 1. The results are provided in FIG. 2.

Figure 2:
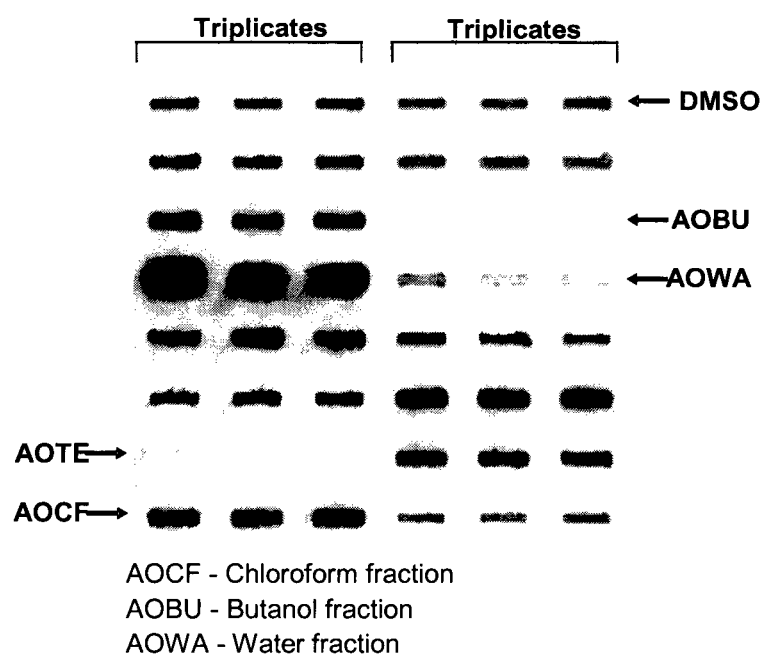
FIG. 2 depicts the results of a Western Blot Analysis of α-synuclein (7 μg) incubated with chloroform (CF), butanol (BU) and water (WA) fractions (50 μg) of the AO extract.

As the results show, the active components were found to reside more in the BU fraction and to a lesser extent in the WA fraction (FIG. 2). The CF fraction was found to have no effect on anti-aggregation activity.

Example 3

The following example illustrates the effect that further subfractions of AO extract have on α-synuclein aggregation activities.

Figure 3:
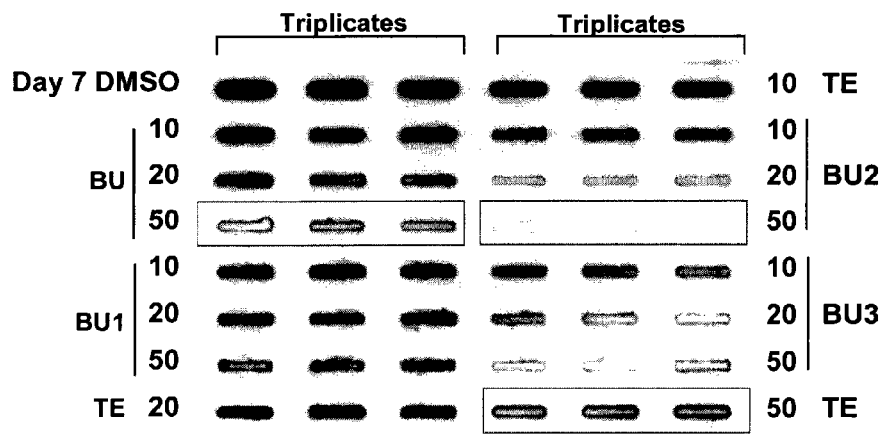
FIGS. 3A and 3B depict the results of a Western Blot Analysis of α-synuclein (7 μg) incubated with butanol (BU) and water (WA) subfractions (10-50 μg) of the AO extract.
Figure 3:
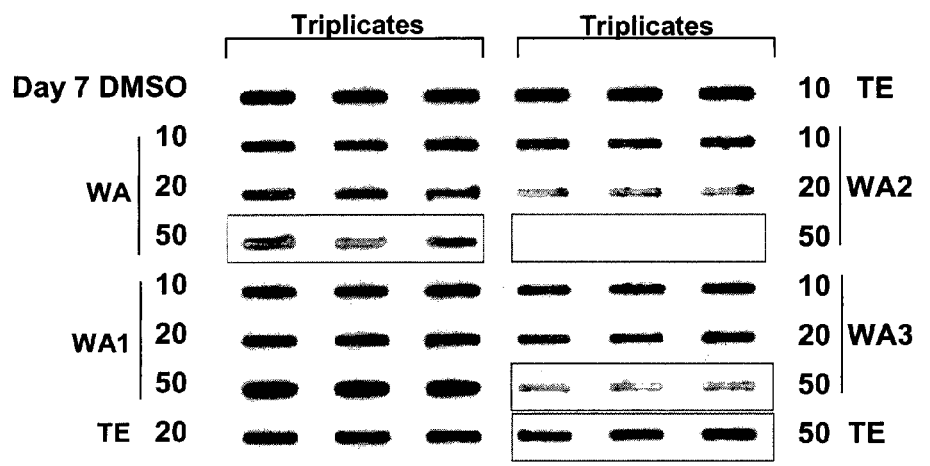

The butanol (BU) and water (WA) fractions of AO from Example 2 were further sub-fractionated into 3 portions using column chromatography eluted with sequential dilutions of ethanol. Each of the subfractions (10-50 μg) was incubated with α-synuclein (7 μg) recombinant protein for 7 days. The assay was performed in triplicate and repeated at least 2 times. Protein was detected as described in Example 1. The results are provided in FIG. 3.

As the results show, the active components of AO are found in BU2, BU3, WA2 and WA3. Active components found were BU2 and BU3 (butanol sub-fraction 2 & 3), WA2 and WA3 (water sub-fractions 2 & 3). BU2 and WA2 showed better anti-aggregative effect than TE when compared at the same dosages.

Example 4

The following example illustrates the effect that further refined fractions of a butanol AO extract have on α-synuclein aggregation activities.

Figure 4:
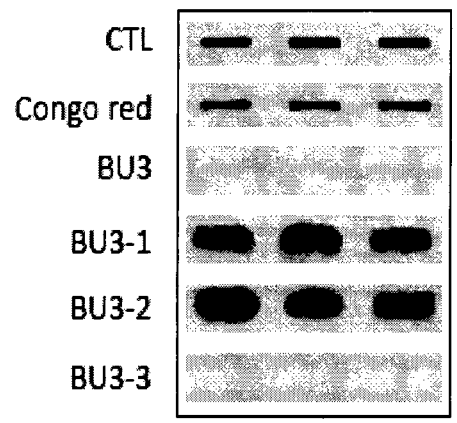
FIGS. 4A and 4B depict the results of a Western Blot Analysis of α-synuclein (7 μg) incubated with butanol (BU) subfractions (10-50 μg) of the AO extract.
Figure 4:
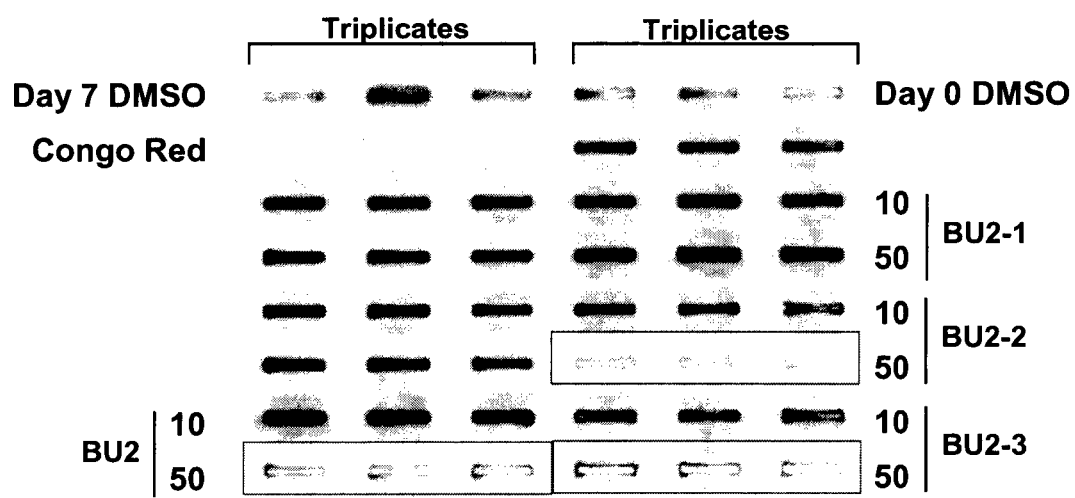

The BU2 and BU3 subfractions of AO extract from Example 3 were further sub-fractionated into 3 fractions by using column chromatography. Each of the subfractions, BU2-1, BU2-2, BU2-3 (10 or 50 μg), BU3-1, BU3-2 and BU3-3 (20 μg) was incubated with α-synuclein (7 μg) recombinant protein for 7 days. Western blot analysis was performed to detect the aggregated α-synuclein. Assay was performed in triplicate and repeated at least 2 times. The results are presented in FIG. 4.

As the results show, the active components of AO were found in BU2-2, BU2-3 and BU3-3.

Example 5

The following example illustrates the use of total extract of *Alpinia officinarum* to protect SH-SY5Y cells against MPP+ excitotoxicity.

A popular PD cell model involves the use of a positively charged molecule, 1-methyl-4-phenylpyridinium (MPP+), with chemical formula $C12H12N^+$. It is a product of the neurotoxin, 1-methyl-4-phenyl-1,2,3,6-tetrahydropyridine (MPTP), converted in the brain by the enzyme MAO-B of glial cells. It causes Parkinson-like symptoms in primates and induces cell death of dopamine-producing neurons in the substantia nigra. Addition of MPP+ to SH-SY5Y cells results in cell death. Therefore, it is a useful model to demonstrate the efficacy of a drug candidate for PD treatment.

SH-SY5Y cells were pretreated with various concentrations of total extract (TE, μg/mL) for 2 hr followed by the co-treatment with MPP+ (50 μM). MTT assay was performed after 3 days incubation. Assay was performed in duplicate and repeated at least 2 times. The results are presented in FIG. 5 as % of control without MPP+ treatment (set as 100% survival). Statistical analysis was performed in comparison to DMSO-treated control (Student T-test), wherein *=$P<0.05$, **=$P<0.005$.

As the results show, total extract of AO at 30 and 50 μg/mL protects SH-SY5Y cells from MPP+ excitotoxicity.

Example 6

The following example illustrates the use of butanol and water fractions of AO to protect SH-SY5Y cells against MPP+ excitotoxicity.

SH-SY5Y cells were pretreated with various concentrations of the chloroform (CF), butanol (BU), and water (WA) fractions (see other examples) for 2 hr followed by the co-treatment with MPP+ (50 μM). Epigallocatechin 3-gallate (EGCG) at 30 μM was used as positive control. MTT assay was performed after 3 days incubation. Assay was performed in duplicate and repeated at least 2 times. Data were presented as % against control without MPP+ treatment (set as 100% survival). Statistic analysis was performed in comparison to DMSO-treated control (Student T-test). *=$P_<0.05$, **=$P<0.005$.

As seen in FIG. 6, the butanol fraction (BU) at 10 μg/mL and water fraction (WA) at 10-50 μg/mL protected SH-SY5Y cells against MPP+ excitotoxicity. While the total extract (TE) of AO at 10 μg/mL shows no protection of cells against MPP+ excitotoxicity, WA and BU at 10 μg/mL shows significant protection, indicating that the fractions are more potent than the extract (TE, FIG. 5)

Example 7

The following example illustrates the use of total extract of *Alpinia officinarum* to protect primary cortical neurons against NMDA excitotoxicity.

Glutamate toxicity represents the secondary drastic neuronal cell death in PD. With the addition of NMDA into the primary cortical neurons, apoptotic cell death occurs through activation of the NMDA subtype glutamate receptors. Therefore, it is a useful model to demonstrate the efficacy of drug candidates targeting glutamate toxicity for PD treatment.

Rat primary neurons were pretreated with total extract (TE, μg/mL) for 2 hr prior to the co-treatment of NMDA for 20 min. Cell death was then measured after 24 hr and detected by LDH assay. Assay was performed in duplicate and repeated at least 2 times. The results are presented in FIG. 7 as % of cell death as compared to vehicle (DMSO)-treated control using one way ANOVA. ***=P<0.005. Memantine at 10 μM was used as positive control.

As the results show, total extract of AO (TE, at 10 μg/mL) significantly protects primary rat cortical neurons from NMDA-induced cell death.

Example 8

The following example illustrates the use of subfractions of total AO extract to protect primary cortical neurons against NMDA excitotoxicity.

Total extract of AO was further sub-fractionated into 3 fractions, chloroform (CF), butanol (BU), and water (WA) (prior Examples). Rat primary neurons were pretreated with the chloroform fraction (CF, μg/mL), butanol fraction (BU, μg/mL), and water fraction (WA, μg/mL) for 2 hr prior to the co-treatment of NMDA for 20 min. Cell death was then measured after 24 hr and detected by LDH assay. Assay was performed in duplicate and repeated for 3 times. The results are presented as % of cell death as compared to vehicle (DMSO)-treated control. Statistical analysis was performed using one way ANOVA. =P<0.01, *=P<0.005.

As the results show, CF at 1 and 10 μg/mL, and BU at 10 μg/mL protect primary cortical neurons against NMDA-induced cell death.

Example 9

The following example illustrates the use of butanol and water subfractions of *Alpinia officinarum* extract to inhibit α-synuclein aggregation in α-synuclein-overexpressing SH-SY5Y cells.

SH-SY5Y cells were transiently transfected with WT-α-syn or mutant α-syn constructs for 48 hr. Cells were then treated with 100 μg/mL total AO extract (AOTE), butanol fraction (AOBU), or water fraction (AOWA) (see other examples). Cell lysates were loaded onto filter trap assay unit and α-synuclein aggregation was detected by Western blot analysis. The results are presented in FIG. 9.

As shown in FIG. 9, treatment with AOTE, AOBU and AOWA at 100 μg/mL reduced aggregated α-synuclein as compared to control.

Example 10

The following example illustrates the use of a butanol fraction of *Alpinia officinarum* extract (AOBU) to reduce 6-hydroxydopamine (6-OHDA) induced α-synuclein oligomerization.

6-OHDA is a potent neurotoxin that causes degeneration of dopaminergic neurons in the substantia nigra and damages nerve endings in the striatum (Breese and Traylor, *J. Pharmacol. Exp. Ther.*, 174: 413-420 (1970)). 6-OHDA has been found in the urine of Parkinson's disease patients (Andrew et al., *Neurochem. Res.*, 18: 1175-1177 (1993)). The toxicity of 6-OHDA involves the generation of a reactive oxygen species as it can autoxidize to form semi-quinone and superoxide anions. However, not only limited to the ROS theory, 6-OHDA has been reported to promote the aggregation in α-synuclein in vitro (Alves da Costa et al., *J. Biol. Chem.*, 281: 9824-9831 (2006)).

AOBU (prior example) was further tested for the inhibitory effect on 6-OHDA-induced α-synuclein aggregation. Recombinant human α-synuclein (1 μg) were incubated with 6-OHDA (50 μg) with or without AOBU (320 μg) for 1-4 hr at 37° C. without shaking. The samples were loaded in each lane of 8% polyacrylamide gel, followed by electrophoretic transfer onto nitrocellulose membranes and Western blot analysis with an anti-α-synuclein monoclonal antibody. An equal amount of protein was loaded in each lane. The amount of 6-OHDA used was equivalent to that applied for intracerebroventricular (i.c.v.) injection in mice. The results are presented in FIG. 10.

As shown in FIG. 10, 6-OHDA gradually induced oligomerization of recombinant human α-synuclein. Following 4-hr incubation with 6-OHDA, high molecular weight α-synuclein aggregates were formed. Co-treatment with AOBU inhibited the formation of high molecular weight α-synuclein aggregates. Results suggest that AOBU inhibited the formation of higher molecular weight α-synuclein aggregates induced by 6-OHDA in vitro.

Example 11

The following example illustrates the use of a butanol fraction of *Alpinia officinarum* extract (AOBU) to rescue TH loss in 6-OHDA injected mice.

6-hydroxydopamine (6-OHDA) is a natural dopaminergic toxin. 3-month-old C57B/6 mice were treated with the butanol fraction of AO (AOBU) (i.p., 10 or 100 mg/kg) daily 5 days before and 3 days after the stereotaxic injection of 6-OHDA (50 μg) into the cerebroventricles of these mice. Striata were collected 3 days after surgery and proteins were extracted for analysis. Tyrosine hydroxylase (TH) loss was determined by Western blot analysis (FIG. 11).

TH is the enzyme responsible for catalyzing the conversion of the amino acid L-tyrosine to dopamine precursor dihydroxyphenylalanine, and serves as an indicator for dopaminergic neurons. Western blot analysis showed that striata from 6-OHDA injected mice had drastically reduced protein expression of TH when compared to ascorbic acid-injected mice (served as sham mice). However, treatment of AOBU at 10 mg/kg or 100 mg/kg restored the TH level in these mice.

Example 12

The following example illustrates the use of a water fraction of *Alpinia officinarum* extract (AOWA) to rescue TH loss in 6-OHDA injected mice.

The experiment described in Example 11 was essentially repeated using the water fraction of AO (AOWA; prepared according to other examples) instead of the butanol fraction (AOBU). In particular, 3-month-old C57B/6 mice were treated with water fraction of AO (AOWA) (i.p., 10 or 100 mg/kg) daily 5 days before and 3 days after the stereotaxic injection of 6-OHDA (50 μg) into the cerebroventricles of the mice. Striata were collected 3 days after surgery. TH loss was determined by Western blot analysis (FIG. 12). The results indicate that treatment of AOWA at 10 mg/kg or 100 mg/kg restored the TH level in these mice.

Example 13

The following Example illustrates the chemical composition of an active butanol fraction of *Alpinia officinarum* extract (AOBU).

The air-dried rhizomes of *Alpinia officinarum* Hance (Zingiberaceae) were harvested at Longtang, Xuwen County, Guangdong Province, China, in August 2009. The air-dried rhizomes of *Alpinia officinarum* (8.0 Kg) were refluxed three times with 70% aqueous EtOH (40 L, 2 hr each). The 70% ethanol extract was concentrated in vacuo to give a residue (TE, 700 g). The residue was suspended in $H_2O$ (1500 mL) and then partitioned successively with chloroform (1500 mL×5) and n-BuOH (1500 mL×5). Evaporation of these fractions resulted in a total of 120 g chloroform extract (CF), 150 g n-BuOH extract (BU), and 400 g water extract (WA).

A part of BU (60 g) was subject to silica gel column chromatography (7×40 cm) using a stepwise gradient elution of dichloromethane, methanol, and water with a ratio of 100:1:0 (2.0 L), 50:1:0 (4.0 L), 20:1:0 (4.0 L), 10:1:0 (4.0 L), 5:1:0 (4.0 L), 3:1:0 (2.0 L), and 10:10:1 (2.0 L) to afford three 66 fractions. Based on the TLC behavior, these fractions were combined and afforded 8 sub-fractions (Fr.A~Fr.H). Compounds 1.1 (800 mg), 1.2 (26 mg) and 1.3 (16 mg) from fraction A, and compound 1.4 (12 mg) from fraction D, were isolated using repetitive column chromatography (silica gel or Sephadex LH-20, finally purity with preparative HPLC). The HPLC chromatograms are presented in FIG. 13.

The structures of these compounds were assigned based on $^1$H NMR, $^{13}$C NMR, DEPT and 2D NMR analysis, as well as chemical experiments (see FIG. 14). The $^1$H and $^{13}$C NMR data of compounds 1.1-1.4 are provided in Table 2 and 3.

TABLE 2

| | 1.1 | | 1.4 | |
|---|---|---|---|---|
| Position | $^1$H NMR | $^{13}$C NMR | $^1$H NMR | $^{13}$C NMR |
| 2 | | 146.6 | | 155.2 |
| 3 | | 137.7 | | 138.8 |
| 4 | | 177.0 | | 178.1 |
| 5 | | 161.9 | | 161.3 |
| 6 | 6.17 (1H, d, J = 1.5 Hz) | 99.4 | 6.08 (1H, d, J = 1.2 Hz) | 98.8 |
| 7 | | 165.3 | | 164.5 |
| 8 | 6.32 (1H, d, J = 1.5 Hz) | 94.6 | 6.32 (1H, d, J = 1.2 Hz) | 93.8 |
| 9 | | 158.1 | | 156.6 |
| 10 | | 104.5 | | 104.5 |
| 1' | | 132.0 | | 130.0 |
| 2' | 8.06 (1H, d, J = 8.0 Hz) | 129.0 | 7.87 (1H, m) | 128.2 |
| 3' | 7.36 (1H, m) | 128.4 | 7.44 (1H, m) | 128.8 |
| 4' | 7.36 (1H, m) | 128.4 | 7.44 (1H, m) | 131.0 |
| 5' | 7.36 (1H, m) | 128.4 | 7.44 (1H, m) | 128.8 |
| 6' | 8.06 (1H, d, J = 8.0 Hz) | 129.0 | 7.87 (1H, m) | 128.2 |
| 3-OCH$_3$ | | | 3.67 (3H, s) | 60.0 |

TABLE 3

| | 1.2 | | 1.3 | |
|---|---|---|---|---|
| Position | $^1$H NMR | $^{13}$C NMR | $^1$H NMR | $^{13}$C NMR |
| 2 | | 147.9 | 4.53 (1H, d, J = 11.7 Hz) | 85.2 |
| 3 | | 137.1 | 5.06 (1H, d, J = 11.7 Hz) | 73.9 |
| 4 | | 178.5 | | 198.2 |
| 5 | | 158.1 | | 165.5 |
| 6 | 6.17 (1H, d, J = 2.0 Hz) | 99.4 | 5.91 (1H, d, J = 1.8 Hz) | 97.7 |
| 7 | | 165.5 | | 168.9 |
| 8 | 6.36 (1H, d, J = 2.0 Hz) | 94.4 | 5.95 (1H, d, J = 1.8 Hz) | 96.6 |
| 9 | | 162.1 | | 164.6 |
| 10 | | 104.5 | | 102.1 |
| 1' | | 123.0 | | 138.7 |
| 2' | 8.15 (1H, d, J = 8.0 Hz) | 130.3 | 7.52 (1H, d, J = 7.6 Hz) | 129.0 |
| 3' | 7.01 (1H, d, J = 8.0 Hz) | 114.7 | 7.37 (1H, m) | 129.6 |
| 4' | | 158.0 | 7.37 (1H, m) | 130.0 |
| 5' | 7.01 (1H, d, J = 8.0 Hz) | 114.7 | 7.37 (1H, m) | 129.6 |
| 6' | 8.15 (1H, d, J = 8.0 Hz) | 130.3 | 7.52 (1H, d, J = 7.6 Hz) | 129.0 |
| 4'-OCH$_3$ | 3.85 (3H, s) | 55.7 | | |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a synucleinopathy in a subject, the method comprising administering to a subject a compound of Formula 1:

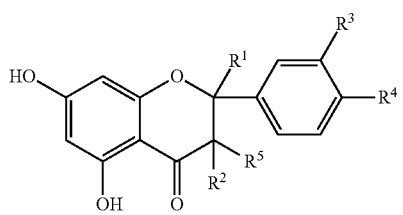

or a salt thereof, wherein

R$^1$ and R$^2$ are both H or together form a bond;

R$^3$ and R$^4$ are independently H or a C$_1$-C$_8$ alkoxy; and

R$^5$ is a C$_1$-C$_8$ alkoxy;

or a compound of Formula 1.3:

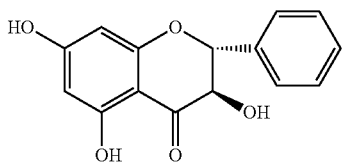

or a salt thereof;
or a combination thereof,
wherein the synucleinopathy is Parkinson's disease (PD).

2. The method of claim 1, wherein the method comprises administering a compound of Formula 1.3 or salt thereof, a compound of Formula 1.4 or salt thereof, or a combination thereof:

1.3

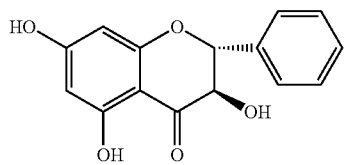 [SMILES: O=C1c2c(O)cc(O)cc2O[C@H](c2ccccc2)[C@H]1O]

1.4

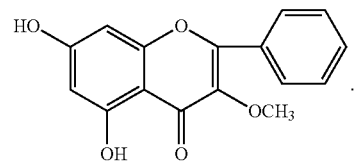 [SMILES: COc1c(-c2ccccc2)oc2cc(O)cc(O)c2c1=O]

3. The method of claim 1, wherein the method comprises administering a compound of Formula 1.3 or salt thereof:

1.3

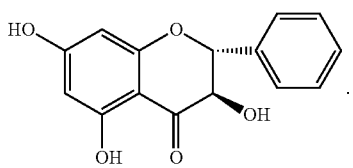

4. The method of claim 1, wherein the method comprises administering a compound of Formula 1.4 or salt thereof:

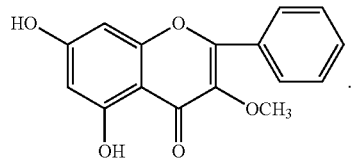

5. The method of claim 1, wherein the method comprises administering a compound of Formula 1.3 or salt thereof and a compound of Formula 1.4 or salt thereof:

1.3

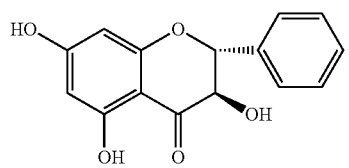

-continued 1.4

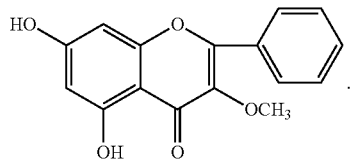

6. A method of inhibiting aggregation of α-synuclein in a subject, the method comprising administering to a subject a compound of Formula 1:

1

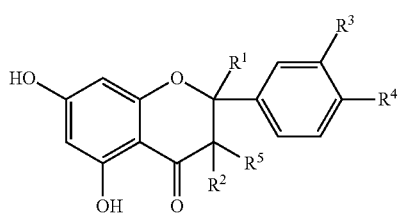

or a salt thereof, wherein
$R^1$ and $R^2$ are both H or together form a bond;
$R^3$ and $R^4$ are independently H or a $C_1$-$C_8$ alkoxy; and
$R^5$ is a $C_1$-$C_8$ alkoxy;
or a compound of Formula 1.3:

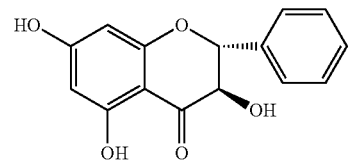

or a salt thereof;
or a combination thereof.

7. The method of claim 6, wherein the method comprises administering a compound of Formula 1.3 or salt thereof, a compound of Formula 1.4 or salt thereof, or a combination thereof:

1.3

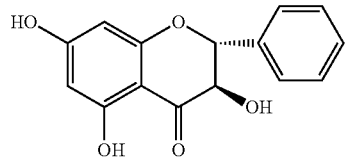

1.4

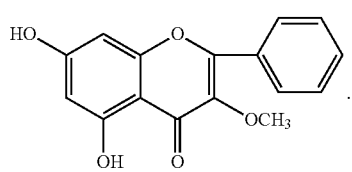

8. The method of claim 6, wherein the method comprises administering a compound of Formula 1.3 or salt thereof:

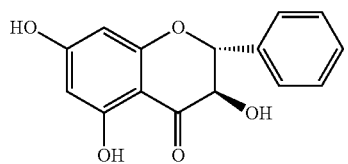 [SMILES: O=C1c2c(O)cc(O)cc2O[C@H](c2ccccc2)[C@H]1O]
1.3
9. The method of claim 6, wherein the method comprises administering a compound of Formula 1.4 or salt thereof:
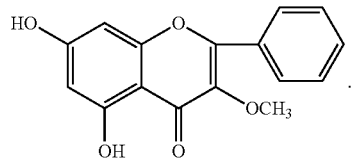
1.4
10. The method of claim 6, wherein the method comprises administering a compound of Formula 1.3 or salt thereof and a compound of Formula 1.4 or salt thereof:
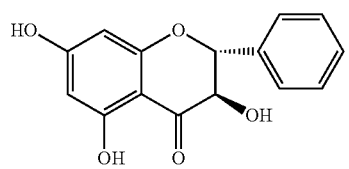
1.3
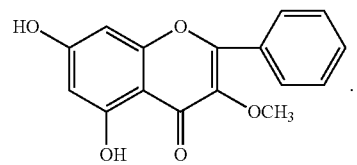 [SMILES: COc1c(-c2ccccc2)oc2cc(O)cc(O)c2c1=O]
1.4
* * * * *